(12) United States Patent
Denis

(10) Patent No.: US 9,232,130 B2
(45) Date of Patent: Jan. 5, 2016

(54) MULTISPECTRAL CAMERA USING ZERO-MODE CHANNEL

(71) Applicant: RAYTHEON CANADA LIMITED, Ottawa (CA)

(72) Inventor: Donald J. Denis, Barrie (CA)

(73) Assignee: RAYTHEON CANADA LIMITED, Ottawa (CA)

( * ) Notice: Subject to any disclaimer, the term of this patent is extended or adjusted under 35 U.S.C. 154(b) by 86 days.

(21) Appl. No.: 14/096,058

(22) Filed: Dec. 4, 2013

(65) Prior Publication Data

US 2015/0156394 A1   Jun. 4, 2015

(51) Int. Cl.

| | |
|---|---|
| *G01J 3/28* | (2006.01) |
| *H04N 5/232* | (2006.01) |
| *G02B 27/28* | (2006.01) |
| *G01J 3/18* | (2006.01) |
| *G01J 3/24* | (2006.01) |
| *G01J 3/447* | (2006.01) |
| *G01N 21/47* | (2006.01) |
| *G01J 3/02* | (2006.01) |

(52) U.S. Cl.
CPC .......... *H04N 5/23212* (2013.01); *G01J 3/0224* (2013.01); *G01J 3/0229* (2013.01); *G01J 3/18* (2013.01); *G01J 3/24* (2013.01); *G01J 3/2823* (2013.01); *G01J 3/447* (2013.01); *G01N 21/4738* (2013.01); *G02B 27/285* (2013.01)

(58) Field of Classification Search
CPC ......... G01J 3/0024; G01J 3/0229; G01J 3/18; G01J 3/24; G01J 3/2823; G01J 3/447; G01N 21/4738; G02B 27/285; H04N 5/23212
See application file for complete search history.

(56) References Cited

U.S. PATENT DOCUMENTS

| | | | |
|---|---|---|---|
| 7,315,371 B2 | 1/2008 | Kryszczynski et al. | |
| 2001/0038451 A1* | 11/2001 | Jung | G01J 3/513 356/328 |
| 2011/0228895 A1* | 9/2011 | Ridley et al. | 378/2 |
| 2012/0008133 A1* | 1/2012 | Silny et al. | 356/73 |
| 2013/0147925 A1* | 6/2013 | Lew et al. | 348/49 |

OTHER PUBLICATIONS

U.S. Appl. No. Entitled "Multispectral Imaging Camera" filed Nov. 1, 2012, 23 pages.

* cited by examiner

*Primary Examiner* — Kara E Geisel
*Assistant Examiner* — Shawn Decenzo
(74) *Attorney, Agent, or Firm* — Lando & Anastasi, LLP

(57) ABSTRACT

A multispectral imaging system and method in which the zero-mode channel is used to provide imaging of any of a variety of optical properties. In one example an imaging method includes spectrally dispersing received electromagnetic radiation into its spectral components with a dispersive element to produce spectrally dispersed electromagnetic radiation, transmitting the electromagnetic radiation through the dispersive element to produce non-dispersed electromagnetic radiation corresponding to a zero order diffraction mode of the dispersive element, imaging the non-dispersed electromagnetic radiation to produce a zero-mode image, and simultaneously imaging the spectrally dispersed electromagnetic radiation to produce a spectral image.

18 Claims, 3 Drawing Sheets

MULTISPECTRAL CAMERA USING ZERO-MODE CHANNEL

BACKGROUND

Hyperspectral cameras are used to detect and analyze the spectral composition of electromagnetic radiation, generally in near ultraviolet, visible, and infrared spectral bands of electromagnetic radiation. Hyperspectral sensors collect information as a set of "images." Each image in the set represents a range of the electromagnetic spectrum referred to as a spectral band. These "images" are combined to form a three-dimensional hyperspectral data cube for processing and analysis. Hyperspectral remote sensing is used in a wide array of applications.

Conventional multispectral imaging systems rely on linear detectors and mirrors or platform motion to move an image across the sensor to capture and record multispectral images. A multispectral image is one that captures image data at specific frequencies across the electromagnetic spectrum. For different purposes, different combinations of spectral bands can be used. Systems relying on scanning mirrors to obtain multispectral images require moving parts. Expensive scanning lasers and custom filters are used in some systems; however, the properties of the filters are fixed at the design time of the instrument, and cannot be easily modified to reconfigure the system to obtain different data. In addition, some systems require multiple sensors and filters, as well as various beamsplitters, to produce multispectral images.

SUMMARY OF INVENTION

Although hyperspectral cameras provide useful spectral imaging data, conventional instruments lack the ability to meaningfully detect other useful optical information, such as polarization or translucence scattering, for example. Aspects and embodiments are directed to a multispectral imaging system that is configured to use the zero-mode channel to detect any of a variety of optical properties, in addition to the traditional spectral imaging data.

According to one embodiment, an imaging system comprises a slit configured to allow incident electromagnetic radiation to enter the imaging system, a dispersive element configured to receive and spectrally disperse the incident electromagnetic radiation into its spectral components to provide spectrally dispersed electromagnetic radiation, and having a zero order mode of diffraction, a focusing optic configured to focus the spectrally dispersed electromagnetic radiation onto an image plane, and further configured to focus non-dispersed electromagnetic radiation corresponding to the zero order mode of the dispersive element onto the image plane, at least one imaging detector positioned at the image plane and configured to produce a spectral image from the spectrally dispersed electromagnetic radiation and a zero-mode image from the non-dispersed electromagnetic radiation, and a filter positioned between the focusing optic and the at least one imaging detector and configured to transmit at least a portion of the non-dispersed electromagnetic radiation to the at least one imaging detector.

In one example the imaging system further comprises a collimator configured to collimate the incident electromagnetic radiation to provide a collimated beam to the dispersive element. The collimator may be a collimating lens, for example. In one example the dispersive element is a diffraction grating. In one example the filter includes a mask. In another example the filter includes a polarizer configured to transmit a first polarization component of the non-dispersed electromagnetic radiation to the at least one imaging detector. In another example the polarizer is a first polarizer, and the filter further comprises a beam splitter configured to separate the non-dispersed electromagnetic radiation into a first optical path and a second optical path, a second polarizer positioned in the second optical path between the beam splitter and the at least one imaging detector and is configured to transmit a second polarization component of the non-dispersed electromagnetic radiation to the at least one imaging detector. In this example the first polarizer is positioned in the first optical path between the beam splitter and the at least one imaging detector, and the first and second polarization components are orthogonal. In one example the first polarization component is horizontal polarization and the second polarization component is vertical polarization. In another example the at least one imaging detector includes a first imaging detector configured to receive and image the spectrally dispersed electromagnetic radiation, and a second imaging detector configured to receive and image the non-dispersed electromagnetic radiation.

According to another embodiment, a multispectral imaging method comprises receiving electromagnetic radiation, spectrally dispersing the electromagnetic radiation into its spectral components with a dispersive element to produce spectrally dispersed electromagnetic radiation, transmitting the electromagnetic radiation through the dispersive element to produce non-dispersed electromagnetic radiation corresponding to a zero order diffraction mode of the dispersive element, imaging the non-dispersed electromagnetic radiation to produce a zero-mode image, and simultaneously imaging the spectrally dispersed electromagnetic radiation to produce a spectral image.

In one example of the method receiving the electromagnetic radiation includes receiving the electromagnetic radiation through a slit. In another example spectrally dispersing the electromagnetic radiation includes spectrally dispersing the electromagnetic radiation corresponding to a first order diffraction mode of the dispersive element to produce the spectrally dispersed electromagnetic radiation. The method may further comprise collimating the electromagnetic radiation prior to spectrally dispersing the electromagnetic radiation, and focusing the non-dispersed electromagnetic radiation and the spectrally dispersed electromagnetic radiation onto an image plane. The method may further comprise filtering the non-dispersed electromagnetic radiation to transmit a first polarization component of the non-dispersed electromagnetic radiation to the image plane and block a second, orthogonal polarization component from reaching the image plane. In another example the method further comprises separating the non-dispersed electromagnetic radiation into first and second orthogonal polarization components, wherein imaging the non-dispersed electromagnetic radiation includes imaging the first and second orthogonal polarization components to obtain polarization information from the non-dispersed electromagnetic radiation.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Aspects and embodiments are directed to a multispectral imaging system that is configured to produce both a conventional three-dimensional multispectral data cube and data related to additional optical properties (such as polarization and translucence, for example) by using the zero-mode channel which is typically ignored in conventional multispectral imagers. As used herein, the term multispectral imager is intended to include both multispectral and multispectral imagers. As discussed in more detail below, according to certain embodiments, a filter is positioned in the optical train of a multispectral imaging system and configured to pass the zero-mode channel to an imaging detector located at the image plane of the system. The filter may have any of numerous configurations, depending, for example, on the optical property to be measured using the zero-mode channel. Using this approach, a multispectral imaging system may be readily configured to provide additional information not available with conventional multispectral imagers, thereby enhancing the utility of the instrument and the data obtained therewith.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 1:
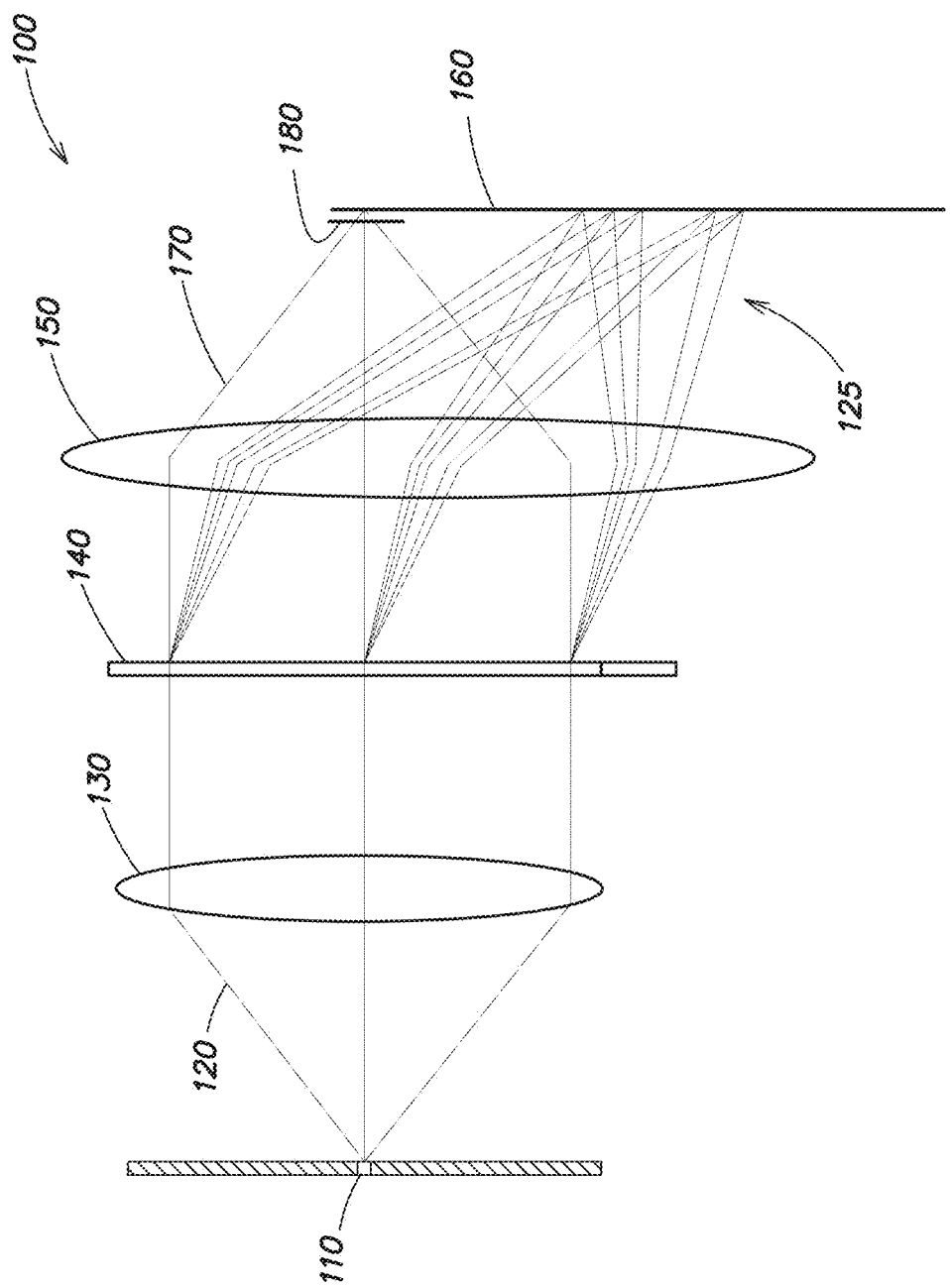
FIG. 1 is a diagram illustrating one example of simplified optics for a spectral imaging system using the zero-mode channel according to aspects of the invention.

Referring to FIG. 1, there is illustrated a simplified optical diagram of one example of a multispectral imaging system using the zero-mode channel according to one embodiment. The system 100 includes a slit 110 through which electromagnetic radiation 120 from an object or distant scene to be imaged enters the imaging system. The slit 110 may include a substrate having an aperture formed therein, and the electromagnetic radiation 120 may pass through the aperture to enter the imaging system. A collimator 130, such as a collimating lens for example, collimates the incoming electromagnetic radiation 120 and passes the collimated beam to a spectrally dispersive element 140. The spectrally dispersive element 140, which may be a diffraction grating, prism, or other dispersive element, disperses the collimated beam of electromagnetic radiation into its spectral components, as schematically illustrated in FIG. 1. A focusing lens 150 focuses the spectrally dispersed electromagnetic radiation 125 onto an imaging detector 160 located at an image plane of the system. In the illustrated example, the spectrally dispersive element 140 is transmissive; however, those skilled in the art will appreciate, given the benefit of this disclosure, that a reflective dispersive element may be used with appropriate modifications to the optical train and placement of the focusing lens 150 and imaging detector 160.

As is known to those skilled in the art, spectrally dispersive elements, such as gratings, for example, may have multiple simultaneous modes or orders of diffraction. In particular, a diffraction grating has a "zero-order mode" in which there is no diffraction. Electromagnetic radiation corresponding to the zero-order mode of diffraction of the dispersive element 140 is represented in FIG. 1 by rays 170, and referred to herein as the zero-mode channel. According to one embodiment, the focusing lens 150 also focuses the electromagnetic radiation 170 of the zero-mode channel onto the imaging detector 160. A filter 180 is positioned in the optical path of the zero-mode channel and configured to act upon the electromagnetic radiation 170 to allow the zero-mode channel to be used to detect and measure any of several optical properties, as discussed further below. In the illustrated example, the focusing lens 150 focuses the electromagnetic radiation 170 onto a portion of the same imaging detector 160 used to image the spectrally dispersed radiation 125. However, in other examples, a separate imaging detector may be used for the zero-mode channel. For example, a two-dimensional focal plane array detector may be used for the spectral imaging (receives and images the dispersed electromagnetic radiation 125), whereas a linear detector may be used for imaging the zero-mode channel.

Figure 2:
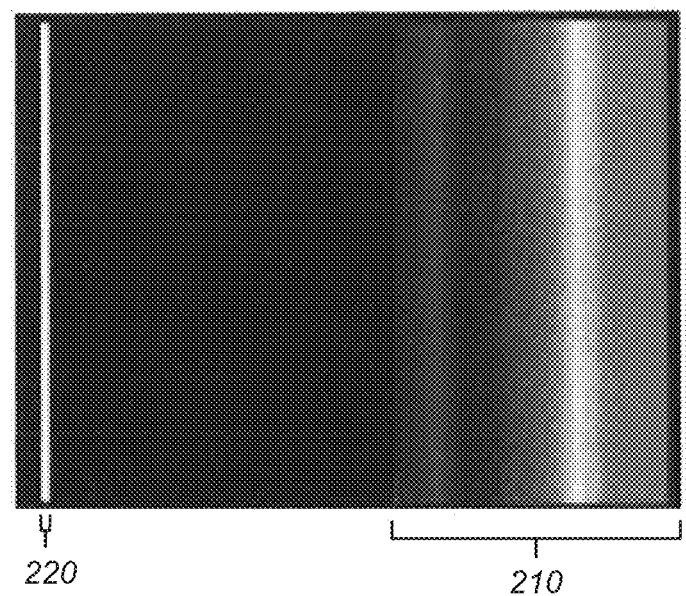
FIG. 2 is a diagram illustrating one example of an imaging detector and filter arrangement according to aspects of the invention.

FIG. 2 illustrates a representation of one example of an image of the slit 110 produced on the imaging detector 160 by collimation (implemented by collimating lens 130), subsequent transmission through a diffraction grating 140, and refocusing onto the image plane (implemented by the focusing lens 150) of the electromagnetic radiation 125 and 170. In this example, the spectral image 210 of the slit 110 is formed on a first region of the imaging detector 160, the spectral imaging being produced from the spectrally dispersed electromagnetic radiation 125. In one example, the first order diffraction mode of the diffraction grating 140 may be used for spectral imaging; however, in other examples, higher order diffraction modes may be used. The zero-mode image 220 of the slit 110 is formed on another region of the imaging detector 160 (or, as discussed above, on a separate detector in some examples), produced by the rays 170 which have passed through the filter 180.

As discussed above, the zero-mode channel may be used to obtain images 220 which may represent, or contain information representing, a variety of optical properties. For example, in certain applications it is desirable to image and measure the translucence of objects, in addition to performing spectral imaging. Therefore, according to one embodiment, the zero-mode channel may be used to obtain translucence information. Translucence appears in an image of an object illuminated with a light spot or line as a broadening of the linewidth of the image of the slit 110 of an appropriate width. Objects that are translucent, such as grapes, for example, "glow" from internal back-scatter when illuminated with a light spot or line. As a result, when imaging using a slit-based spectrometer, such as the imaging system of FIG. 1, the detector 160 receives not only the return beam from the laser, but also surrounding light from the "glow" caused by the object's translucence. Thus, for example referring to FIG. 2, instead of the zero-mode image 220 appearing as a single line along one or more rows or columns of pixels of the detector 160, the line may be broadened, with one or more rows or columns of pixels to either side of the central return beam recording some intensity level representative of the translucence of the imaged object. In this example, the filter 180 may be omitted to pass the electromagnetic radiation 170 to the imaging detector 160. In this instance, the rows or columns of pixels containing the main return beam are ignored or zeroed, and the broader image containing the information of interest is retrieved, summed, and/or averaged from neighboring rows/columns. Those skilled in the art will appreciate, given the benefit of this disclosure, that the detector 160 may be positioned such that "rows" become "columns" and vice versa, or may be positioned at an angle such that the rows or columns are not necessarily arranged perpendicular to the detector's surface normal. Accordingly, the use herein of the terms rows and columns is intended to be illustrative and for purposes of explanation, and is not intended to limit the detector 160 to any particular orientation.

Alternatively, the filter 180 may include a mask that masks the main return beam from the illuminated object, and allows the spread return light caused by the translucence of the object to pass through to the imaging detector. This configuration may be advantageous in certain examples because the signal-to-noise ratio of the translucence measurements may be improved by blocking the main return beam.

According to another embodiment, the zero-mode channel may be used to measure polarization. In this embodiment, the dispersive element 140 may be a polarization-maintaining volume transmission grating, or other dispersive element that does not affect the polarization of the transmitted (or reflected) electromagnetic radiation 170. In this example, the filter 180 includes one or more polarizers that pass specified polarization components (e.g., horizontal or vertical polarization, or left-hand or right-hand circular polarization) of the electromagnetic radiation 170 through to be imaged by the imaging detector 160.

Figure 3:
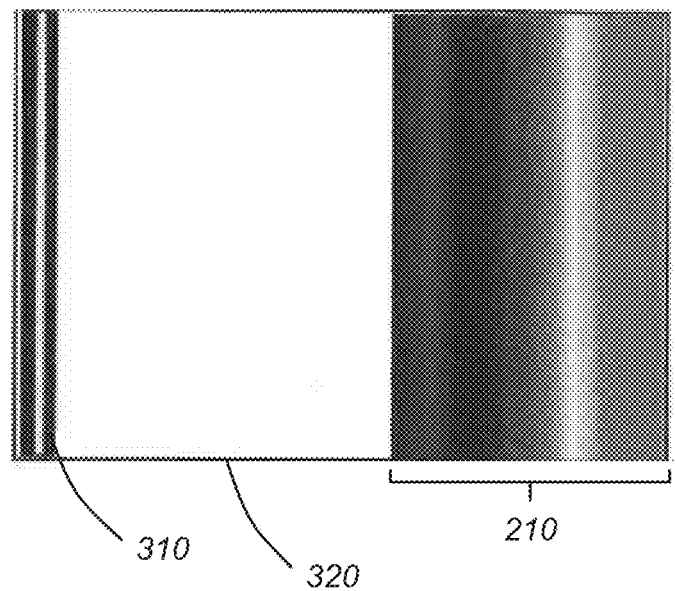
FIG. 3 is a diagram illustrating another example of an imaging detector and filter arrangement, including a polarization filter on the zero-mode channel, according to aspects of the invention.

For example, referring to FIG. 3, the filter 180 may include a polarizer 310 that is positioned over a few columns or rows of pixels of an imaging detector 320. This allows these pixels to collect polarization information from the zero-mode channel electromagnetic radiation 170, as discussed above. The imaging detector 320 further includes a region that receives the spectrally dispersed electromagnetic radiation 125 and produces the spectral image 210, as discussed above. Thus, the imaging system may simultaneously, and independently, collect spectral and polarization information by using the zero-mode channel. The same slit and majority of the optical train is used for both types of imaging (spectral and polarization), thereby avoiding registration errors that often occur when separate instruments are used to obtain the different images.

Figure 4:
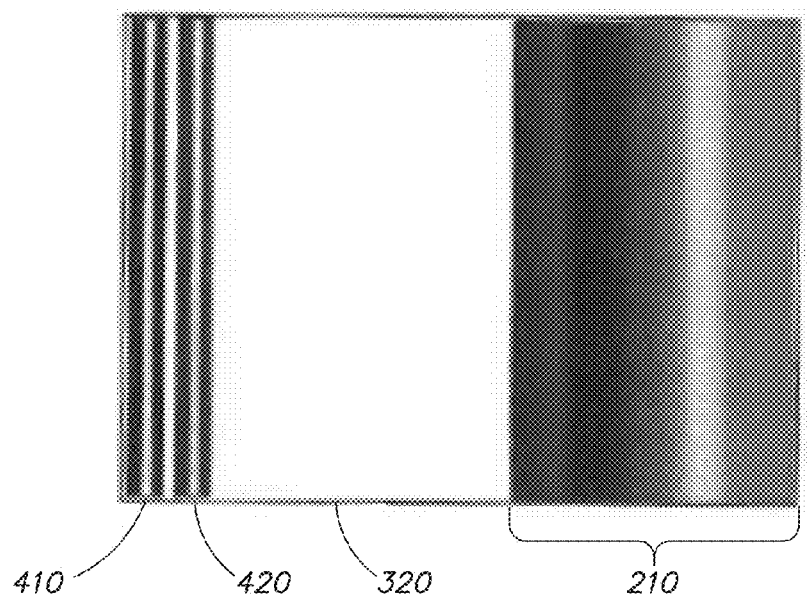
FIG. 4 is a diagram of another example of an imaging detector and filter arrangement, including dual polarization filters on the zero-mode channel, according to aspects of the invention.

In the example illustrated in FIG. 3, the filter 180 includes a single polarizer, and the system may therefore image single type of polarization (for example, horizontal or vertical). According to another embodiment, the filter 180 may include dual polarizers to allow simultaneous imaging of both horizontal and vertical (or right-hand and left-hand circular) polarizations, as illustrated in FIG. 4. In this example, the filter 180 includes a first polarizer 410 positioned over a few rows or columns of pixels of the imaging detector 320, and a second polarizer 420 positioned over a nearby or adjacent few rows or columns of pixels. The first polarizer may be a horizontal polarizer and the second polarizer may be a vertical polarizer, for example, or vice versa. It will be appreciated by those skilled in the art that although in FIGS. 3 and 4, the region of the detector to the left of the spectral image is shown in white (to allow the filters to be more clearly seen in the diagram), in actuality, this region may be black, as shown in FIG. 2.

Figure 5:
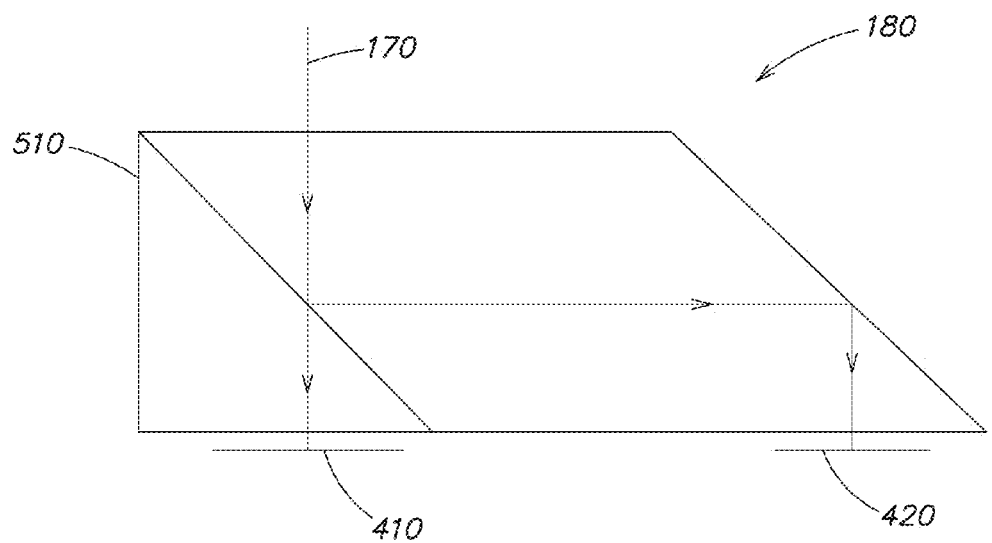
FIG. 5 is a diagram of one example of a dual filter arrangement according to aspects of the invention.

FIG. 5 is a schematic diagram illustrating one example of a configuration of the filter 180 to achieve dual polarization imaging on the zero-mode channel, as discussed above with reference to FIG. 4. In this example, the filter 180 includes a beam splitting prism 510 that splits the incoming electromagnetic radiation 170 into two optical paths. The first and second polarizers 410 and 420 are coupled to the prism 510 and each receive a portion of the electromagnetic radiation 170, as shown in FIG. 5. In certain applications, it be may preferable that the prism 510 is relatively small, particularly with respect to the depth of field of the imaging detector 320, such that the optical path length difference between the two polarization components is not so large as to cause one of the imaged components to be out of focus. In one example, the filter 180 of FIG. 5 may be fabricated using micro-deposition techniques, optionally similarly to the manner in which lenslet arrays are constructed. The configuration of FIG. 5 is one example that allows imaging of orthogonal polarizations on the zero-mode channel. However, as will be appreciated by those skilled in the art, given the benefit of this disclosure, there are numerous other types and configurations of filters that may be used, and the example of FIG. 5 is not intended to be limiting.

Thus, aspects and embodiments provide a system and method by which to use the zero-mode channel of a multi-spectral imaging system, which is conventionally ignored or discarded, to perform additional imaging functions simultaneously with spectral imaging and using a single instrument. As discussed above, some examples of optical properties which may be measured using the zero-mode channel include translucence and polarization; however, any of several imaging functions may be performed. The filter 180 may be tailored for specific applications; for example, the filter may include a mask or one or polarizers, as discussed above. The filter 180 may be interchanged with filters configured for different applications to reconfigure the multispectral imaging system for different functions. For example, a filter 180 including a mask for translucence measurements may be replaced with a filter including a polarizer for polarization measurements, without necessarily requiring any other modifications to the optical train of the multispectral imaging system.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. An imaging system for imaging a translucent object, the imaging system comprising:
    a slit configured to allow incident electromagnetic radiation to enter the imaging system;
    a dispersive element configured to receive and spectrally disperse the incident electromagnetic radiation into its spectral components to provide spectrally dispersed electromagnetic radiation, the dispersive element having a zero order mode of diffraction;
    a focusing optic configured to focus the spectrally dispersed electromagnetic radiation onto an image plane, and further configured to focus non-dispersed electromagnetic radiation corresponding to the zero order mode of the dispersive element onto the image plane, the non-dispersed electromagnetic radiation including a main beam; and
    at least one imaging detector positioned at the image plane and configured to produce a spectral image from the spectrally dispersed electromagnetic radiation and a zero-mode image from the non-dispersed electromagnetic radiation, the zero-mode image including an indication of a translucence of the translucent object, the at least one imaging detector including an array of pixels configured to receive the non-dispersed electromagnetic radiation, a first plurality of pixels of the array of pixels configured to receive at least a portion of the non-dispersed electromagnetic radiation excluding the main beam, the first plurality of pixels further configured to measure intensity of the portion of the non-dispersed electromagnetic radiation, the intensity being representative of the translucence of the translucent object.

2. The imaging system of claim 1, further comprising a collimator configured to collimate the incident electromagnetic radiation to provide a collimated beam to the dispersive element.

3. The imaging system of claim 2, wherein the collimator is a collimating lens.

4. The imaging system of claim 1, wherein the dispersive element is a diffraction grating.

5. The imaging system of claim 1, wherein the at least one imaging detector includes:
    a first imaging detector configured to receive and image the spectrally dispersed electromagnetic radiation; and
    a second imaging detector configured to receive and image the non-dispersed electromagnetic radiation, the second imaging detector including the array of pixels.

6. The imaging system of claim 1, wherein the array of pixels is a two-dimensional array including a plurality of rows and columns of pixels, at least one row of pixels configured to receive the main beam of the non-dispersed electromagnetic radiation, and wherein the first plurality of pixels includes at least one row of pixels on either side of the at least one row of pixels configured to receive the main beam.

7. The imaging system of claim 6, wherein the at least one imaging detector is configured to exclude the at least one row of pixels configured to receive the main beam from the zero-mode image.

8. The imaging system of claim 1, wherein the array of pixels is a two-dimensional array including a plurality of rows and columns of pixels, at least one column of pixels configured to receive the main beam of the non-dispersed electromagnetic radiation, and wherein the first plurality of pixels includes at least one column of pixels on either side of the at least one column of pixels configured to receive the main beam.

9. The imaging system of claim 8, wherein the at least one imaging detector is configured to exclude the at least one column of pixels configured to receive the main beam from the zero-mode image.

10. The imaging system of claim 1, further comprising a mask configured to block the main beam of the non-dispersed electromagnetic radiation from reaching the array of pixels.

11. The imaging system of claim 1, further comprising an illuminator configured to illuminate the translucent object with an illumination beam.

12. An imaging method for imaging a translucent object, the imaging method comprising:
    receiving electromagnetic radiation;
    spectrally dispersing the electromagnetic radiation into its spectral components with a dispersive element to produce spectrally dispersed electromagnetic radiation;
    transmitting the electromagnetic radiation through the dispersive element to produce non-dispersed electromagnetic radiation corresponding to a zero order diffraction mode of the dispersive element, the non-dispersed electromagnetic radiation including a main beam;
    imaging the non-dispersed electromagnetic radiation with an imaging detector including an array of pixels to produce a zero-mode image, including recording an intensity of the non-dispersed electromagnetic radiation excluding the main beam using a first plurality of pixels of the array of pixels to provide in the zero-mode image a representation of translucence of the translucent object; and
    simultaneously imaging the spectrally dispersed electromagnetic radiation to produce a spectral image.

13. The imaging method of claim 12, wherein receiving the electromagnetic radiation includes receiving the electromagnetic radiation through a slit.

14. The imaging method of claim 12, wherein spectrally dispersing the electromagnetic radiation includes spectrally dispersing the electromagnetic radiation corresponding to a first order diffraction mode of the dispersive element to produce the spectrally dispersed electromagnetic radiation.

15. The imaging method of claim 12, further comprising:
    collimating the electromagnetic radiation prior to spectrally dispersing the electromagnetic radiation; and
    focusing the non-dispersed electromagnetic radiation and the spectrally dispersed electromagnetic radiation onto an image plane, the imaging detector being located at the image plane.

16. The imaging method of claim 12, wherein imaging the non-dispersed electromagnetic radiation further includes receiving the main beam of the non-dispersed electromagnetic radiation at a second plurality of pixels of the array of pixels, and excluding the second plurality of pixels from the zero-mode image.

17. The imaging method of claim 12 further comprising filtering the non-dispersed electromagnetic radiation to block the main beam from reaching the imaging detector.

18. The imaging method of claim 12 further comprising illuminating the translucent object with an illumination beam.

\* \* \* \* \*